United States Patent
Langevin

[11] Patent Number: 6,030,631
[45] Date of Patent: Feb. 29, 2000

[54] DEVICE AND METHOD FOR DECREASING NAUSEA AND VOMITING

[75] Inventor: Paul B. Langevin, Gainesville, Fla.

[73] Assignee: University of Florida, Gainesville, Fla.

[21] Appl. No.: 09/025,135

[22] Filed: Feb. 18, 1998

Related U.S. Application Data

[60] Provisional application No. 60/038,661, Feb. 21, 1997.

[51] Int. Cl.[7] .................................................. A01N 25/34
[52] U.S. Cl. ............................................................ 424/402
[58] Field of Search ...................................... 424/402, 404

[56] References Cited

U.S. PATENT DOCUMENTS

| | | |
|---|---|---|
| 4,296,104 | 10/1981 | Hershchler .............................. 424/153 |
| 5,558,874 | 9/1996 | Haber et al. ............................. 424/402 |
| 5,730,991 | 3/1998 | Rapaport ................................. 424/401 |

*Primary Examiner*—Jose' G. Dees
*Assistant Examiner*—Kathryne E. Shelborne
*Attorney, Agent, or Firm*—Saliwanchik, Lloyd & Saliwanchik

[57] ABSTRACT

The subject invention relates to devices that are specifically designed to safely and efficiently administer alcohol vapor for innocuous insufflation or inhalation, and to related methods of administering alcohol in this manner. The subject invention is preferably used to treat a patient suffering from post-operative nausea or vomiting that are side effects that often accompany the use of anesthetics for surgical applications.

14 Claims, 2 Drawing Sheets

DEVICE AND METHOD FOR DECREASING NAUSEA AND VOMITING

CROSS-REFERENCE TO A RELATED APPLICATION

The subject application claims priority to provisional patent application Ser. No. 60/038,661, filed Feb. 21, 1997.

BACKGROUND OF THE INVENTION

Nausea and emesis are often induced by stimulation of either the chemoreceptor trigger zone or the emesis (or vomiting) center in the central nervous system. Such stimulation can be caused by afferent stimulation (e.g., tactile pharyngeal impulses, labrynthine disturbances, motion, increased intracranial pressure, pain, distention of viscera or psychologic factors) or blood born emetic substances (e.g., as seen during pregnancy, cancer chemotherapy, uremia, radiation therapy, electrolyte and endocrine disturbances, or the presence of chemical emetic substances). Nausea and vomiting are also common post-operative side effects that result from the use of anesthetics. These symptoms are known as post-operative nausea and vomiting (PONV).

A series of medication alternatives are currently used to combat PONV. The drugs used most frequently are benzamides (e.g. Metoclopramide),phenothiazines(e.g. Phenergan) and Serotonin inhibitors (e.g. Ondancetron). In order to minimize the side effects, these drugs are most often administered in this sequence. If Metroclopramide fails to produce adequate relief, Phenergan is administered. If sufficient relief is still not experienced, Ondancetron is given to the patient. In efforts to control cost and potential side effects, these medications are usually given in sequence at 30 minute intervals. This methodology can significantly prolong the time the patient remains in the recovery room, an area of the hospital where every additional minute represents enormous expense.

The most common side effects of metroclopramide, which are experienced by about 10% of treated patients involve the central nervous system (CNS) and include restlessness, fatigue, drowsiness and lassitude. Insomnia, headache and dizziness occur less frequently. Delirium, severe dysphoria, obsessive rumination, mania, depression, and suicidal indication have also been reported. Extrapyramidal effects also result from dopaminergic blockage. This usually presents in the form of akathisia and occurs most often in children and young adults. Dystonic reactions resembling acute dyskinesia occur in less than 1% of young patients receiving low doses of Metroclopramide, but occur as often as in 25% of patients receiving higher doses.

Phenergan (a phenothiazine derivative) is frequently the second line drug for treating PONV. In addition to producing all the side effects of other antihistamines, phenothiazines have their own side effects. These stem in part from the anticholinergic effects of the drug and include dry mouth, blurred vision, confusion and delirium. Extrapyramidal side effects include lassitude, inco-ordination, tinnitus, diplopia, excitation, nervousness, seizure and catatonia. Bradycardia and hypotension have also been reported with rapid intravenous administration. Promethazine is a chemical irritant and extravasation has resulted in necrotic lesions. Venous thrombosis is an additional potential side effect.

The serotonin inhibitors represent a new class of anti-emetics that are normally well tolerated by most patients. Studies comparing the incidence of the side effects of Ondancetron vs. Metoclopramide indicate that Ondancetron produces a higher incidence of headache (17.25%) and constipation (3%), while Metoclopramide produces diarrhea and extrapyramidal symptoms more frequently. Twelve percent of patients who were administered Ondancetron for PONV complained of dizziness, 8% complained of sedation and drowsiness, 5% complained of malaise or fatigue and 2% complained of paresthesia. Pruritus has been reported in 2% of patients receiving Ondancetron. Hypersensitivity reactions typically occur when repeated dosages are administered in efforts to control PONV. Cardiovascular side effects are rare but when experienced are serious and usually occur at dosages used for chemotherapy induced nausea and vomiting.

Droperidol is sometimes used for PONV and can be quite effective. Unfortunately, the use of this drug tends to significantly prolong the recovery room stay due to the associated excessive sedation. The drug can produce profound dysphoria. Extrapyramidal effects have also been reported with some regularity.

The plethora of drugs that are used in efforts to treat PONV demonstrates their relative ineffectiveness in producing relief. The serotonin inhibitors while being more effective, unfortunately remain expensive. In addition, patients who are experiencing PONV usually have IV access. These medications are typically given parenterally to insure delivery and to hasten their onset. Hence, they share the risks associated with any parenteral drug, such as error, infection, overdose, extravasation, in addition to the added expense.

In summary, the drugs currently being used to treat PONV are often ineffective and can ultimately demand the use of all three types of medications, produce undesirable and in some cases high risk side effects, require administration by skilled nursing personnel (an added expense), significantly increase the time patients remain in the recovery room, and are themselves expensive.

Anti-emetic devices that are specifically designed to easily, safely, and efficiently administer alcohol to a person have not been previously disclosed or suggested.

BRIEF SUMMARY OF THE INVENTION

The subject invention relates to devices that are specifically designed to safely and efficiently administer alcohol vapor for innocuous insufflation or inhalation, and to related methods of administering alcohol in this manner. The subject invention is preferably used to treat a patient suffering from post-operative nausea or vomiting that are side effects that often accompany the use of anesthetics for surgical applications.

The devices disclosed herein preferably comprise an adhesive strip; a pad or a dressing centrally located on the adhesive strip, wherein said dressing is treated with alcohol, preferably isopropyl alcohol; and an impervious material that covers the dressing and serves as a physical barrier to prevent direct contact between the dressing (and the alcohol which it contains) and the skin of a person treated with the subject device.

The subject invention also relates to methods of using devices, such as those described herein, for decreasing nausea and vomiting, preferably post-operative nausea and vomiting.

The numerous unexpected advantages provided by the subject device, as discussed herein, will be apparent to the skilled artisan in light of the present disclosure.

BRIEF DESCRIPTION OF THE DRAWINGS

For a better understanding of the present invention, reference will be made to the following detailed description of the invention which is to be read in conjunction with the following drawings, wherein.

DETAILED DISCLOSURE OF THE INVENTION

The subject invention relates to devices that are specifically designed to safely and efficiently administer alcohol vapor for innocuous insufflation or inhalation, and to related methods of administering alcohol in this manner. The subject invention is preferably used to treat a patient suffering from post-operative nausea or vomiting that are side effects that often accompany the use of anesthetics for surgical applications.

Figure 1:
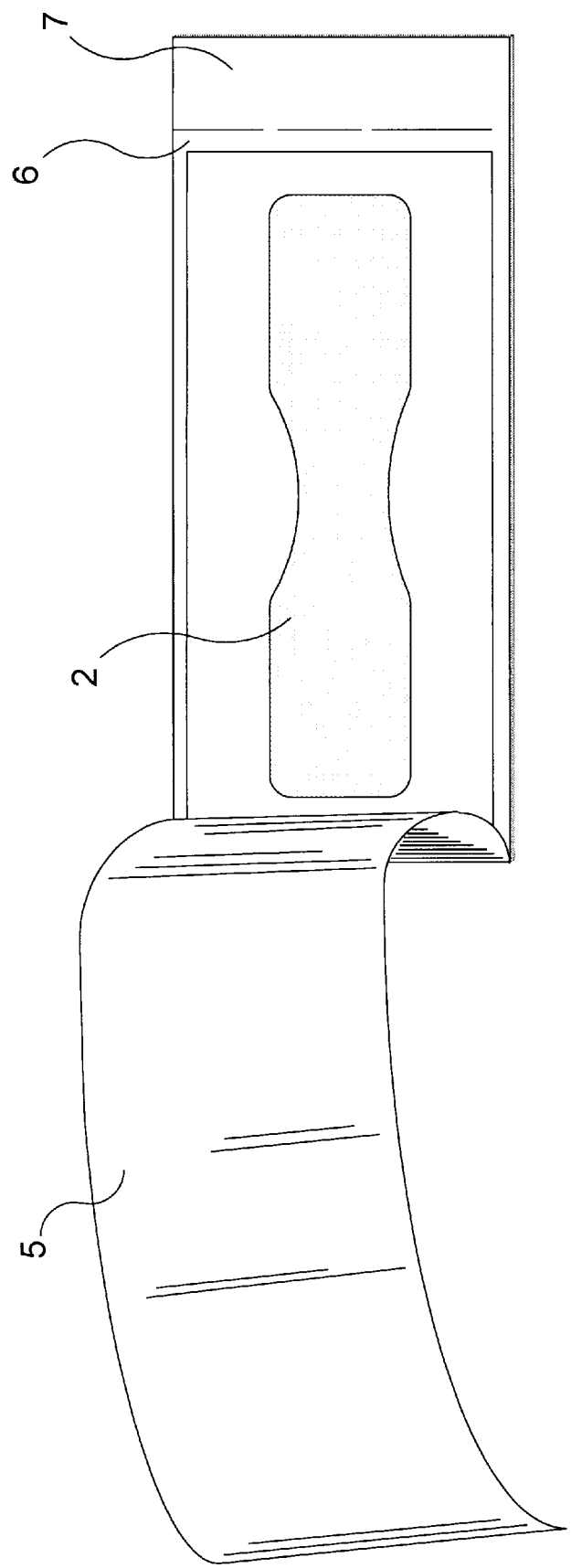
FIG. 1 is a top view of a specific embodiment of a device of the subject invention in a foil package.
Figure 2:
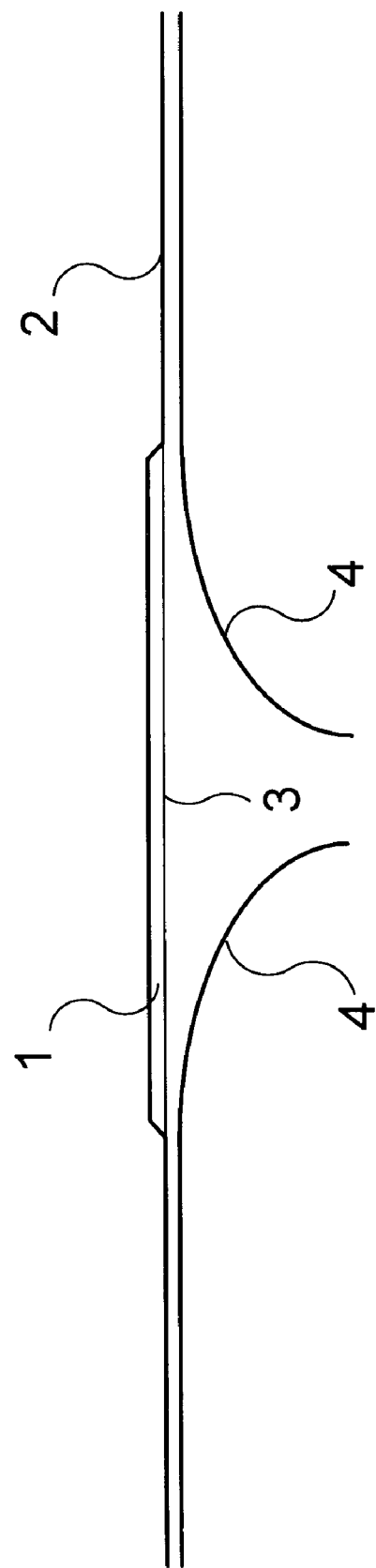
FIG. 2 is a longitudinal cross section of a preferred device according to the subject invention.

A specific embodiment of the device of the subject invention can comprise the following components: an adhesive strip, an alcohol-treated pad or a dressing attached to the adhesive strip, and a non-porous, non-adhesive surface on the pad. Referring to FIGS. 1 and 2, which depict a specific embodiment of the subject invention, the alcohol-treated pad 1 is centrally located on a breathable adhesive strip 2. The pad 1 and the adhesive strip 2 each typically have two sides. As shown in FIG. 2, the top side of the pad 1 is attached to the bottom side of the adhesive strip. A non-porous, nonadhesive surface 3 is on the bottom side of the pad 1.

When applied to a person in order to prevent or reduce nausea and/or vomiting, the pad is typically placed just under the person's nostrils and the exposed adhesive surfaces on either end of the adhesive strip are applied and attached, via the adhesive, to either side of the treated person's labium. The subject device can be left in place until the nausea and vomiting are relieved.

In a preferred embodiment, the adhesive strip 2 is a segment of breathable adhesive tape having a porous surface. As used herein, "breathable" means that the material allows the skin covered underneath to remain exposed to the air. One advantage of this arrangement is that the porosity will allow the skin to "breath" when it is covered by the adhesive portion of this preferred embodiment of the subject device. The non-porous, non-adhesive surface 3 serves as a physical barrier to prevent direct contact between the dressing (and the alcohol which it contains) and the skin of a person treated with the subject device. Alcohol can irritate the skin if the skin is exposed to the alcohol for extend periods of time. This arrangement allows the alcohol in the pad to be insufflated through the breathable adhesive tape, on the side of the device located away from the skin, by the person experiencing nausea or vomiting. Although the foregoing is the preferred arrangement, other arrangements are contemplated.

Isopropyl alcohol (Isopropanol) is the most preferred alcohol for use according to the subject invention. Other alcohols, such as ethyl alcohol (ethanol), may also be used. Preferably, the pad is saturated with 3–5 ml of 70% isopropyl alcohol.

In light of the subject disclosure, the skilled artisan will be able to routinely select and use various materials not specifically mentioned herein, for constructing the subject device. For example, the pad can be made of cotton or a cotton blend. Various plastics and adhesives can be used in the construction of the adhesive strip, as would be well known in the art in light of the subject disclosure. In addition, although the subject device can be constructed in various shapes and sizes, the skilled artisan, having the benefit of the subject disclosure, can select dimensions of the subject device that would be optimal for use on humans, as suggested herein. For example, the adhesive strip 2 and the pad 1, is preferably biconvex in the center so that it can be applied to the labellum under the bridge of the nose without contacting the vermillion border of the upper lip, as shown in FIG. 1.

For ease of packaging and to facilitate convenient use, a peel-away backing 4, as shown in FIG. 2, will preferably be removably affixed to each of the exposed adhesive ends of the adhesive strip 2 and will cover the non-porous, non-adhesive surface 3 on the pad 1. In addition, the subject device will typically be packaged in an airtight foil package 5. A seal 6 in the package 5 will typically be used to keep the subject device in a sealed environment within the package 5 so as to prevent the alcohol in the pad from evaporating until the subject device is to be used. Preferably, the subject device and the package 5 are sterilized during manufacture so that the subject device is contained in a sterile environment inside the seal 6 within the package 5.

In the preferred embodiment as shown in FIG. 1, the package 5 has two halves. When ready for use, the subject device can be removed from the typical package 5 by grasping a free tab 7 on each half of the package and pulling the package apart, thereby breaking the seal 6. The peel-away backings 4 can then be removed from the adhesive strip 2, and the subject device is ready to be applied to the nose of a person experiencing nausea or vomiting.

With the benefit of the present disclosure, one skilled in the art could readily construct and use the devices of the subject invention. Techniques and materials that are well known in the art could be used or adapted to produce the subject anti-emetic devices.

Those skilled in the medical arts and the art of biomedical devices will readily perceive various other useful variations and applications for the devices of the present invention. The skilled artisan would also know of various ways in which such devices can be incorporated into conventional and state of the art anti-emetic regimens, in light of the subject disclosure. While the foregoing description of the invention and examples of specific embodiments thereof teach the skilled artisan how to make and use devices according to the subject invention, including its best mode, it should be understood that equivalents and obvious variations of the specifics disclosed herein form an integral part of this invention.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. An alcohol-insufflation device for treating nausea or vomiting wherein said device comprises a means for holding alcohol near the nostrils of a person being treated for nausea or vomiting without directly contacting said alcohol with the skin of the person being treated, wherein said device comprises an alcohol-saturated pad attached to an adhesive strip.

2. The device, according to claim 1, wherein said pad has a first side and a second side, wherein said first side of said pad is attached to said strip, and wherein said device comprises a non-porous, non-adhesive surface on said second side of said pad.

3. The device, according to claim 2, wherein said strip has a central portion and two end portions, wherein said pad is attached to the central portion of said strip, and wherein said pad and the central portion of said strip are biconvex.

4. The device, according to claim 3, wherein said strip is breathable.

5. The device, according to claim 3, wherein said alcohol is selected from the group consisting of isopropanol or ethanol.

6. A method for treating nausea or vomiting comprising attaching a pad, wherein said pad is saturated with alcohol, near the nostrils of a person suffering from nausea or vomiting without directly contacting the alcohol to the skin of the person.

7. The method, according to claim 6, wherein said alcohol is selected from the group consisting of isopropanol or ethanol.

8. A method for treating a person suffering from post-operative nausea or vomiting, wherein said method comprises attaching to the face of the person a device that comprises an alcohol-saturated pad attached to an adhesive strip, and leaving said device attached to the face of the person for a period of time sufficient to reduce the nausea or vomiting.

9. The method, according to claim 8, wherein said alcohol is selected from the group consisting of isopropanol or ethanol.

10. The method according to claim 6 wherein said pad comprises a non-porous, non-adhesive surface.

11. The method according to claim 6 wherein said pad is biconvex.

12. The method according to claim 8 wherein said device comprises a non-porous, non-adhesive surface on said pad.

13. The method according to claim 8 wherein at least a portion of said device is biconvex.

14. The method according to claim 13 wherein a central portion of said strip is biconvex.

* * * * *

UNITED STATES PATENT AND TRADEMARK OFFICE
CERTIFICATE OF CORRECTION

PATENT NO. : 6,030,631
APPLICATION NO. : 09/025135
DATED : February 29, 2000
INVENTOR(S) : Paul B. Langevin It is certified that error appears in the above-identified patent and that said Letters Patent is hereby corrected as shown below:

Column 4, line 60 (Claim I):

"An alcohol-insufflation device for treating nausea or vomiting wherein said device comprises a means for holding alcohol near the nostrils of a person being treated for nausea or vomiting without directly contacting said alcohol with the skin of the person being treated, wherein said device comprises an alcohol-saturated pad attached to an adhesive strip."

should read

--An alcohol-insufflation device for treating nausea or vomiting wherein said device comprises a means for holding alcohol near the nostrils of a person being treated for nausea or vomiting without directly contacting said alcohol with the skin of the person being treated, wherein said device comprises an alcohol-saturated pad attached to an adhesive strip, and wherein said pad has a width that allows for placement of said pad under the nose and above the vermillion border of the upper lip of the person treated with said device--.

Column 5, line 12 (Claim 6):

"A method for treating nausea or vomiting comprising attaching a pad, wherein said pad is saturated with alcohol, near the nostrils of a person suffering from nausea or vomiting without directly contacting the alcohol to the skin of the person."

should read

--A method for treating nausea or vomiting comprising attaching a pad, wherein said pad is saturated with alcohol, near the nostrils of a person suffering from nausea or vomiting without directly contacting the alcohol to the skin of the person, and wherein said pad has a width that allows for placement of said pad under the nose and above the vermillion border of the upper lip of the person treated with said device.--

UNITED STATES PATENT AND TRADEMARK OFFICE
CERTIFICATE OF CORRECTION

PATENT NO.        : 6,030,631
APPLICATION NO.   : 09/025135
DATED             : February 29, 2000
INVENTOR(S)       : Paul B. Langevin It is certified that error appears in the above-identified patent and that said Letters Patent is hereby corrected as shown below:

Column 6, line 3 (Claim 8):

"A method for treating a person suffering from post-operativenausea or vomiting, wherein said method comprises attaching to the face of the person a device that comprises an alcohol-saturated pad attached to an adhesive strip, and leaving said device attached to the face of the person for a period of time sufficient to reduce the nausea or vomiting."

should read

--A method for treating a person suffering from post-operative nausea or vomiting, wherein said method comprises attaching to the face of the person a device that comprises an alcohol-saturated pad attached to an adhesive strip, and leaving said device attached to the face of the person for a period of time sufficient to reduce the nausea or vomiting, and wherein said pad has a width that allows for placement of said pad under the nose and above the vermillion border of the upper lip of the person treated with said device.--

Signed and Sealed this

Thirty-first Day of July, 2007

JON W. DUDAS
*Director of the United States Patent and Trademark Office*